US008343947B2

(12) United States Patent
Messadek

(10) Patent No.: US 8,343,947 B2
(45) Date of Patent: Jan. 1, 2013

(54) THERAPEUTIC TREATMENT

(76) Inventor: Jallal Messadek, Liege (BE)

( * ) Notice: Subject to any disclaimer, the term of this patent is extended or adjusted under 35 U.S.C. 154(b) by 65 days.

(21) Appl. No.: 12/726,109

(22) Filed: Mar. 17, 2010

(65) Prior Publication Data

US 2010/0210608 A1    Aug. 19, 2010

Related U.S. Application Data

(63) Continuation of application No. 11/333,514, filed on Jan. 17, 2006, now abandoned, which is a continuation-in-part of application No. PCT/BE2004/000101, filed on Jul. 8, 2004.

(30) Foreign Application Priority Data

Jul. 15, 2003 (BE) .................................. 2003/0408

(51) Int. Cl.
*A61K 31/585* (2006.01)
*A61K 31/185* (2006.01)
*A01N 37/00* (2006.01)

(52) U.S. Cl. ........................................ 514/175; 514/578

(58) Field of Classification Search .................. 514/175, 514/578
See application file for complete search history.

(56) References Cited

U.S. PATENT DOCUMENTS

| | | | |
|---|---|---|---|
| 3,577,534 A | 5/1971 | Koh et al. |
| 4,066,756 A | 1/1978 | Orr et al. |
| 4,140,755 A | 2/1979 | Sheth et al. |
| 4,605,548 A | 8/1986 | Ushiyama et al. |
| 4,703,045 A | 10/1987 | Guinot |
| 4,814,179 A | 3/1989 | Bolton |
| 4,902,718 A | 2/1990 | Bayless et al. |
| 4,911,916 A | 3/1990 | Cleary |
| 4,968,719 A * | 11/1990 | Brevetti ......................... 514/556 |
| 5,217,997 A | 6/1993 | Levere et al. |
| 5,342,621 A | 8/1994 | Eury |
| 5,405,614 A | 4/1995 | D'Angelo et al. |
| 5,716,941 A | 2/1998 | Rabinoff |
| 5,814,599 A | 9/1998 | Mitragotri et al. |
| 5,876,780 A | 3/1999 | Virtanen et al. |
| 5,880,098 A | 3/1999 | Haussinger |
| 5,928,195 A | 7/1999 | Malamud et al. |
| 5,961,999 A | 10/1999 | Bimczok et al. |
| 6,008,221 A * | 12/1999 | Smith et al. ..................... 514/250 |
| 6,056,958 A | 5/2000 | Mousa |
| 6,228,875 B1 | 5/2001 | Tsai et al. |
| 6,235,311 B1 | 5/2001 | Ullah et al. |
| 6,287,765 B1 | 9/2001 | Cubicciotti |
| 6,355,166 B1 | 3/2002 | Amarasinghe et al. |
| 6,399,785 B1 | 6/2002 | Murphy et al. |
| 6,476,006 B2 | 11/2002 | Flashner-Barak et al. |
| 6,504,005 B1 | 1/2003 | Fridkin et al. |
| 6,531,171 B2 | 3/2003 | Armand et al. |
| 6,624,180 B2 | 9/2003 | South et al. |
| 6,762,025 B2 | 7/2004 | Cubicciotti |
| 6,855,734 B2 | 2/2005 | Messadek |
| 6,881,420 B2 | 4/2005 | Flashner-Barak et al. |
| 7,097,968 B2 | 8/2006 | Yuan et al. |
| 7,608,640 B2 | 10/2009 | Messadek |
| 7,780,990 B2 | 8/2010 | Messadek |
| 7,786,077 B2 | 8/2010 | Messadek |
| 2002/0065320 A1 | 5/2002 | Messadek |
| 2002/0183380 A1 | 12/2002 | Hunter |
| 2002/0193307 A1 | 12/2002 | Banting et al. |
| 2003/0054978 A1 | 3/2003 | Babish |
| 2003/0124705 A1 | 7/2003 | Berry et al. |
| 2003/0170223 A1 | 9/2003 | Ahmad |
| 2003/0203385 A1 | 10/2003 | Venkataraman et al. |
| 2003/0203878 A1 | 10/2003 | Flashner-Barak et al. |
| 2004/0043442 A1 | 3/2004 | Jutila et al. |
| 2004/0067986 A1 | 4/2004 | Sassover |
| 2004/0072750 A1 | 4/2004 | Phillips et al. |
| 2005/0013866 A1 | 1/2005 | Maincent et al. |
| 2005/0239719 A1 | 10/2005 | Zeldis |
| 2006/0034918 A1 | 2/2006 | Messadek |
| 2006/0128657 A1 | 6/2006 | Messadek |
| 2006/0160896 A1 | 7/2006 | Messadek |
| 2006/0233877 A1 | 10/2006 | Messadek et al. |
| 2007/0134324 A1 | 6/2007 | Messadek |
| 2007/0213399 A1 | 9/2007 | Messadek |
| 2009/0286881 A1 | 11/2009 | Messadek |
| 2010/0004199 A1 | 1/2010 | Messadek |
| 2010/0221330 A1 | 9/2010 | Messadek |

FOREIGN PATENT DOCUMENTS

| | | |
|---|---|---|
| BE | 1012546 | 12/2000 |
| BE | 1012712 | 2/2001 |
| BE | 20030248 | 4/2003 |
| DE | 19910682 | 9/2000 |
| EP | 0347864 | 12/1989 |
| EP | 0349902 | 1/1990 |
| EP | 0781554 | 7/1997 |
| FR | 2590 M | 6/1964 |
| FR | 7047549 | 8/1972 |
| FR | 7729075 | 9/1977 |

(Continued)

OTHER PUBLICATIONS

Anonymous (The medical letter of drugs and therapeutics (1997) 39: p. 12).*
Malinow (Clinical Chemistry (1994) 40:173-176).*
Bio Ethic (Antithrombotic effect of Betaine, Jan. 2003).*
Hiatt (International Journal of Clinical Practice (2001) 119:20-27).*
Andersson et. al. (Genetics in Medicine (1999) 1:146-150).*
Office Action dated Dec. 8, 2011 in related U.S. Appl. No. 12/558,973, filed Sep. 14, 2009.
Office Action dated Apr. 20, 2012 in related U.S. Appl. No. 12/868,592, filed Aug. 25, 2010.
Office Action dated Jan. 13, 2012 in related U.S. Appl. No. 11/747,167, filed May 10, 2007.
Office Action dated Jul. 27, 2010 in related U.S. Appl. No. 12/558,973, filed Sep. 14, 2009.
Office Action dated Mar. 1, 2011 in related U.S. Appl. No. 12/558,973, filed Sep. 14, 2009.

(Continued)

*Primary Examiner* — Marcos Sznaidman

(57) ABSTRACT

The invention describes the use of betaine for treating and preventing arterites. The invention also describes an orally administered composition for treating arterites and, in particular, intermittent claudication, said composition containing, as an active ingredient, an active therapeutic quantity of betaine glycine by single dose. The invention particularly describes a medicament provided for treating a patient suffering from an intermittent claudication caused by peripheral circulatory disorders such as arteriosclerosis obliterans or by thromboangiitis obliterans.

12 Claims, No Drawings

FOREIGN PATENT DOCUMENTS

| | | |
|---|---|---|
| HU | 210122 B | 9/1992 |
| JP | 2000143486 | 5/2000 |
| WO | 9515750 | 6/1995 |
| WO | 9706795 | 2/1997 |
| WO | 9738685 | 10/1997 |
| WO | 9738686 | 10/1997 |
| WO | 9819690 | 5/1998 |
| WO | 9856497 | 12/1998 |
| WO | 9945913 | 9/1999 |
| WO | WO 00/25764 * | 5/2000 |
| WO | 0051596 | 9/2000 |
| WO | 0156609 | 8/2001 |
| WO | 0200213 | 1/2002 |
| WO | 0212704 | 1/2002 |
| WO | 0247493 | 6/2002 |
| WO | 02062322 | 8/2002 |
| WO | 02066002 | 8/2002 |
| WO | 03187074 | 10/2003 |
| WO | 2004032916 | 4/2004 |
| WO | 2004096499 | 5/2004 |
| WO | 2004049095 | 6/2004 |
| WO | 2004091601 | 10/2004 |
| WO | 2005004854 | 1/2005 |
| WO | 2005011642 | 2/2005 |
| WO | 2005011645 | 2/2005 |
| WO | 2005065675 | 7/2005 |
| WO | 2006007671 | 1/2006 |
| WO | 2006050581 | 5/2006 |
| WO | 2006050585 | 5/2006 |

OTHER PUBLICATIONS

Lacy et al., Drug Information Handbook, 7th Edition 1999-2000, p. 140.

Lacy et al., Drug Information Handbook, 7th Edition 1999-2000, pp. 285-286.

Office Action dated Aug. 24, 2011 in related U.S. Appl. No. 11/747,167, filed May 10, 2007.

Office Action dated Dec. 14, 2011 in related U.S. Appl. No. 12/704,294, filed Feb. 11, 2010.

Office Action dated Jun. 9, 2011 in related U.S. Appl. No. 12/510,034, filed Jul. 27, 2009.

Office Action dated Mar. 26, 2012 in related U.S. Appl. No. 12/704,294, filed Feb. 11, 2010.

Office Action dated Apr. 24, 2012 in related U.S. Appl. No. 12/783,377, filed May 19, 2010.

Office Action dated Sep. 6, 2011 in related U.S. Appl. No. 11/625,448, filed Jan. 22, 2007.

Remington, "The Science and Practice of Pharmacy," 19th Edition, 1995, Chapter 91, p. 1612, Mack Publishing Company.

Search Report dated Dec. 6, 2004 in corresponding PCT/BE2004/000101 (WO2005/004854).

Written Opinion dated May 3, 2005 in corresponding PCT/BE2004/000101 (WO2005/004854); WIPO English translation.

International Preliminary Report on Patentability dated Jan. 16, 2006 in corresponding PCT/BE2004/000101 (WO2005/004854); WIPO English translation.

Varga et al., "Homocysteine and MTHFR Mutations: Relation to Thrombosis and Coronary Artery Disease," American Heart Association, 2005, 111:e289-e293.

Albert et al., "Effect of Folic Acid and B Vitamins on Risk of Cardiovascular Events and Total Mortality Among Women at High Risk for Cardiovascular Disease: A Randomized Trial," JAMA. 2008, 299(17):2027-2036.

Office Action dated Nov. 10, 2011 in related U.S. Appl. No. 12/510,034, filed Jul. 27, 2009.

Office Action dated Feb. 2, 2011 in related U.S. Appl. No. 11/625,448, filed Jan. 22, 2007.

Office Action dated Apr. 17, 2008 in related U.S. Appl. No. 11/251,737, filed Oct. 17, 2005.

Office Action dated Sep. 20, 2007 in related U.S. Appl. No. 11/333,514, filed Jan. 17, 2006.

Office Action dated Nov. 15, 2007 in related U.S. Appl. No. 11/333,514, filed Jan. 17, 2006.

McGregor et al, "A Controlled Trial of the Effect of Folate Supplements on Homocysteine, Lipids and Hemorheology in End-State Renal Disease," Nephron, vol. 85, No. 3, 2000, 215-220.

Gurfinkel et al., "Fast platelet suppression by lysine acetylsalicylate in chronic stable coronary patients. Potential clinical impact over regular aspirin for coronary syndromes," Clin. Cardiol., Sep. 2000;23(9):697-700.

Klasing et al., "Dietary Betaine Increases Intraepithelial Lymphocytes in the Duodenum of Coccidia-Infected Chicks and Increases Functional Properties of Phagocytes," 2002, The American Society for Nutritional Sciences, J. Nutr, 132:2274-2282, 2002.

Schmidt et al., "Total nitric oxide production is low in patients with chronic renal disease," Kidney International, 2000, 58, 1261-1266.

Letter Regarding Dietary Supplement Health Claim for Folic Acid, Vitamin B6, and Vitamin B12 and Vascular Disease, to Jonathan W. Emord of Emord & Associates, PC, from Christine J. Lewis of the FDA, Nov. 28, 2000.

Zollei, I. et al., Betaine-Palmitate Reduces Acetylsalicyclic Acid-induced Gastric Damage in Rats, Scand J. Gastroenterol 2001 (8), pp. 811-816.

Al Awami et al., "Homocysteine levels in patients with Raynaud's phenomenon," Vasa. May 2002; 31(2): 87-90.

Stammler et al., "The prevalence of hyperhomocysteinemia in thromboangitis obliterans. Does homocysteine play a role pathogenetically?" Dtsch Med Wochenschr, Nov. 15, 1996;121(46):1417-23.

McCarty, "Co-administration of equimolar doses of betaine may alleviate the hepatotoxic risk associated with niacin therapy," Med-Hypothesis, Sep. 2000; 55(3): 189-94.

Letter regarding Petition for Health Claim: Folic Acid, Vitamin B6, and Vitamin B12 Dietary Supplements and Vascular Disease, to Jonathan W. Emord of Emord & Associatees from Christine J. Lewis of the FDA, Feb. 9, 2001.

Birnie et al., "Antimicrobial Evaluation of N-Alkyl Betaines and N-Alkly-N,N-Dimethylamine Oxides with Variations in Chain Length," Antimicrobial Agents and Chemotherapy, Sep. 2000, p. 2514-2517.

Karoly, Palatka et al., "Changes in the expression and distribution of the inducible and endothelial nitric oxide synthase in mucosal biopsy specimens of inflammatory bowel disease," Scandinavian Journal of Gastroenerology, 2005, vol. 40, No. 6, pp. 670-680.

Van Hoek, "Non-alcoholic fatty liver disease: a brief review," Scandinavian Journal of Gastroenerology Supplement, 2004;(241):56-9.

Mendes et al., "Recent advances in the treatment of non-alcoholic fatty liver disease," Expert Opin. Investig. Drugs, Jan. 2005;14(1):29-35.

Hiatt et al, Long-term safety of cilostazol in patients with peripheral artery disease: The CASTLE study (Cilostazol: A Study in Long-term Effects), Journal of Vascular Surgery, vol. 47, No. 2, pp. 330-336, Feb. 2008.

Korzh, "Relationship Between Endothelial Nitric Oxide Synthesis and Low-Grade Chronic Inflammation," European Atherosclerosis Society, 73rd EAS Congress, Salzburg, Austria, Jul. 7-10, 2002.

Didier et al., "Distal cutaneous necrosis, an unusual etiology: hyperhomocysteinemia," Ann Dermatol Venereol, Nov. 1999;126(11):822-5; PMID: 10612875.

Gurfinkel et al., "Fast Platelet Suppression by Lycine Acetylsalicylate in Chronic Stable Coronary Patients. Potential Clinical Impact Over Regular Aspirin for Coronary Syndromes," Abstracts—Myocardiol Ischemia and Infarction, JACC, Feb. 2000, 408A-409A.

Bonaa et al., Homocysteine lowering and cardiovascular events after acute myocardial infarction,: N. Eng. J. Med., Apr. 13, 2006; 354(15):1578-88. Epub Mar. 12, 2006.

Lonn et al., "Homocysteine lowering folic acid and B vitamins in vascular disease," N. Eng. J. Med., Apr. 13, 2006;354 (15):1567-77. Epub Mar. 12, 2006.

Approval of Cilostazol, Jan. 6, 2006, Center for Drug Evaluation and Research, www.fda.gov/cder/news/cilostazol/appproval.htm.

Diagnosis and Management of Peripheral Arterial Disease: A National Clinical Guideline, Scottish Intercollegiate Guidelines Network, Oct. 2006, www.sign.ac.uk.

Hiatt, "Medical Treatment of Peripheral Arterial Disease and Claudication," N Engl J Med, vol. 344, No. 21, May 24, 2001, pp. 1608-1621.

Hiatt, "The US experience with cilostazol in treating intermitten claudication," Atherosclerosis Supplements 6 (2006) 21-31.

Carman and Fernandez, "A Primary Care Approach to the Patient with Claudication," American Family Physician, vol. 61, No. 4, Feb. 15, 2000, http://www.aafp.org/afp/20000215/1027.html, 8 pages.

Beaufour and Beaufour, "Nouvelles associations antinévralgiques à tolérance améliorée," Brevet Spécial De Médicament, P.V. No. 927.734, No. 2.590, 1964, pp. 1-5.

Feb. 23, 1996 Chinese document (pp. 91-93) with English translation titled "Homocysteine and Vascular Disease," 5 pages.

Da Silva and Sobel, Abstract from Entrez-PubMed web page entitled "Anicoagulants: to bleed or not to bleed, that is the question," Semin Vasc. Surg. Dec. 2002;15(4):256-67, 1 page.

JACC Abstracts, Myocardial Ischemia and Infarction, Feb. 2000, 1196-107, pp. 408-409.

Lasch, H.G., Abstract from Entrez-PubMed web page entitled "Principles of Drug Prevention of Thrombosis," Langenbecks Arch Chir., 1986;369:451-7, 1 page.

Marcel et al., Abstract from Entrez-PubMed web page entitled "From Virchow to red cells (the unended quest).", Ric Clin Lab., 1983;13 Suppl 3:71-81, 1 page.

Office Action dated Sep. 20, 2007 in related U.S. Appl. No. 10/635,048, filed Aug. 4, 2003.

Office Action dated Dec. 21, 2006 in related U.S. Appl. No. 10/635,048, filed Aug. 4, 2003.

Office Action dated Nov. 5, 2002 in related U.S. Appl. No. 09/945,391, filed Aug. 31, 2001.

Office Action dated Jun. 4, 2003 in related U.S. Appl. No. 09/945,391, filed Aug. 31, 2001.

Office Action dated Dec. 6, 2005 in related U.S. Appl. No. 10/635,048, filed Aug. 4, 2003.

Savi et al., Abstract from Entrez-PubMed web page entitled "SR 121787, a new orally active fibrinogen receptor antagonist," Thromb Haemost, Sep. 1998;80(3):469-76., 1 page.

Banno et al., Abstract from Entrez-PubMed web page entitled "Antiaggregatory, antithrombotic effects of MS-180, a novel platelet glycoprotein IIb/IIIa receptor antagonist," Eur J Pharmacol., Feb. 19, 1999;367(2-3):275-82., 1 page.

Ramjit et al., Abstract from Entrez-PubMed web page entitled "Antithrombotic effects of MK-0852, a platelet fibrinogent receptor antagonist, in canine models of thrombosis," J Pharmacol Exp Ther., Sep. 1993;266(3):1501-11, 2 pages.

Hoffmann et al., Abstract from Entrez-PubMed web page entitled "Prevention of thrombosis and enhancement of thrombolysis in rabbits by SR 121787, a glycoprotein II/III antagnoist," J Pharmacol Exp Ther., Aug. 1998;286 (2):670-5., 1 page.

Packham, Abstract from Entrez-PubMed web page entitled "Role of platelets in thrombosis and hemostasis." Can J Physiol Pharmacol., Mar. 1994;72(3):278-84., 1 page.

Lynch et al., Abstract from Entrez-PubMed web page entitled "Nonpeptide glycoprotein IIb/IIIa inhibitors. 5. Antithrombotic effects of MK-0383," J Pharmacol Exp Ther., Jan. 1995;272(1):20-32., 2 pages.

Katada et al., Abstract from Entrez-PubMed web page entitled "The in vitro and in vivo pharmacological profiles of a platelet glycoprotein IIb/IIIa antagonist, NSL-9403," Thromb Res., Oct. 1, 1997;88(1):27-70., 1 page.

Ogawa et al., Abstract from Entrez-PubMed web page entitled "Antiplatelet and antithrombotic effects of orbofiban, a new orally active GPIIb/IIIa antagonist, in guinea pigs," Thromb Res., Mar. 1, 2000;97(5):307-15., 1 page.

Zapadniuk, Abstract from Entrez-PubMed web page entitled "Cholagogic effect of trimethylglycine in normal animals of different ages and in experimental atherosclerosis," Biull Eksp Biol Med., Jul. 1987;104(7):30-2., 2 pages.

Panteleimonova, Abstract from Entrez-PubMed web page entitled "Effect of trimethylglycine on lipid metabolism in experimental atherosclerosis in rabbits," Farmakol Toksikol, Jul.-Aug. 1983;46(4):83-5., 1 page.

Fazio et al., "Treatment of Human Atherosclerosis with Betaine," Minerva Med, Apr. 25, 1961, pp. 1511-1516.

P.H. List et al., "Hagers Handbuch Der Pharmazeutischen Praxis," 1972, Pringer Verlag, Berlin Heidelberg, New York, p. 431.

Wilcken et al., "The natural history of vascular disease in homocystinuria and the effects of treatment," J. Inher. Metab. Dis. 20(1997) 295-230.

Swan M.A., Improved Preservation of Ultrastuctural Morphology in Human Spermatozoa Using Betaine in the Primary Fixative, Int. J. Androl., Feb. 20, 1997 (1): 45-54, PMID: 9202990, 1 page.

Reynolds, Betaine Hydrochloride, Matindale, The Extra Pharmacopoeia, 1996, Royal Pharmaceutical Society, London, p. 1679.

1225. Betaine, The Merck Index, 1996 Merck and Co., Whithouse Stations, NJ, p. 198.

Mar et al., Abstract from Entrez-PubMed web page entitled "Betaine in wine: answer to the French paradox?" Med Hypotheses, Nov. 1999;53(5):383-5., 2 pages.

Salamone et al, "Changes in blood coagulation in experimental subacute poisoning with p-dichlorobenzene. The influence of some lipotropic factors," Journal, Answer 13 of 13, Copyright 2003, ACS, 1 page.

Vinson et al., "New Drug Approvals of 1996-Part 3," Drug Topics, Mar. 17, 1997, University of Mississippi School of Pharmacy, pp. 72-81.

Matthews et al., An indirect response model of homocysteine suppression by betaine: optimising the dosage regimen of betaine in homocystinuria,: 2002 Blackwell Scient Ltd Br J Clin Pharmacol, 54, 140-146.

Schwahn et al, "Pharmacokinetics of oral betaine in healthy subjects and patients with homocystinuria," 2003 Blackwell Scient Ltd Br J Clin Pharmacol, 55, 6-13.

Bandfield et al., "Naproxen, Naproxen Sodium, and Naproxen Betainate Sodium Monohydrate Salts," Pharmaceutics 1, Apr. 14, 2001, pp. 1-5.

Van Hecken et al., Abstract from Entrez-PubMed web page entitled "Effect of clopidogrel on naproxen-induced gastrointestinal blood loss in healthy volunteers," Drug Metabol Drug Interact, 1998;14(3):193-205., 1 page.

EC-Naprosyn, Naprosyn, Anaprox, Naprosyn, Rx Only, Roche Pharmaceuticals, Copyright 1999-2004 by Roche Laboratories Inc., pp. 1-20.

Environmental and Health Assessment of Substances in Household Detergents and Cosmetic Detergent Products, Environment Project, 615, 2001, 6.1 Betaines, http:www2.mst.dk/common/Udgivramme/Frame.asp?pg=http://www2.mst.dk/udgiv/Publications/2001/87-7944-596-9/html/helepubl_eng.htm, 1 page.

Wyrick P.B. et al., The Microbicidal Agent C31G Inhibits Chlamydia Trachomatis Infectivity in vitro., Antimicrob Agents Chemother, Jun. 1997 41(6): 1335-44, PMID: 9174195, 1 page.

Thompson, K.A. et al., Assessment of the Anti-Microbial Agent C31G as a Spermicide: Comparison with Nonoxynol-9, Contraception, May 1996 53(5): 313-8, PMID: 8724622, 1 page.

Rogers J.S., Abstract from Entrez-PubMed web page entitled "Hypercoagulable states," W V Med J., Feb. 1993;89 (2):61-3, 1 page.

Nielsen H.K., Abstract from Entrez-PubMed web page entitled "Pathophysiology of venous thromboembolism," Semin Thromb Hemost, 1991;17 Suppl 3:250-3, 1 page.

Silver et al., Abstract from Entrez-PubMed web page entitled "The caput medusae of hypercoagulability," J. Vasc. Surg., Feb. 2000;31(2):396-405, 1 page.

Swan M.A., "Improved Preservation of the Ram Spermatozoan Plasma Membrane using Betaine in the Primary Fixative," J. Microsc., Sep. 1997 187(pt 3): 167-9, PMID: 9351233, 1 page.

Thomas, K.C. et al., Effects of Particulate Materials and Osmoprotectants on Very-High-Gravity Ethanolic Fermentaiont by *Saccharomyces cerevislae*, Appl Environ Microbiol, May 1994, 60(5): 1519-24, PMID: 801734, 1 page.

Chambers, S. et al., The Osmoprotective Properties of Urine for Bacteria: The Protective Effect of Betaine and Human Urine Against Low pH and High Concentrations of Electrolytes, Sugars, and Urea, J. Infect Dis., Dec. 1985, 152 (6): 1308-16, PMID: 3905988, 1 page.

Smith, L.T., Role of Osmolytes in Adaptation of Osmotically Stressed and Chill-Stressed Listeria Monocytogenes Grown in Liquid Media and on Processed Meat Surfaces, Appl Environ Microbiol, Sep. 1996 62(9): 3088-93, PMID: 8795194, 1 page.

Peddie B.A. et al., Is the Ability of Urinary Tracy Pathogens to Accumulate Glycine Betaine a Factor in the Virulence of Pathogenic Strains?, J. Lab. Clin. Med., Oct. 1996 128(4): 417-22, PMID: 8833891, 1 page.

Koskinen, E. et al., A Preliminary Study on the Use of Betaine as a Cryoprotective Agent in Deep Freezing of Stallion Semen, Zentralbl Veterinarmed A., Feb. 1989, 36(2): 110-4, PMID: 2501949, 1 page.

Bidulescu et al., Usual choline and betaine dietary intake and incident coronary heart disease: the Atherosclerosis Risk in Communities (ARIC) Study,BMC Cardiovasc Disord. 2007, 7:20.

Hallas et al., "Use of single and combined antithrombotic therapy and risk of serious upper gastrointestinal bleeding: population based case-control study," BMJ 2006;333:726, Oct. 7, 2006.

Cassar, "Intermittent Claudication," BMJ, vol. 333, Nov. 11, 2006, pp. 1002-1005.

Apgar, "Efficacy of Cilostazol for Intermittent Claudication," American Family Physician, Feb. 15, 2000, 2 pages.

Girolami et al., "Treatment of Intermittent Claudication with Physical Training, Smoking Cessation, Pentoxifylline, or Nafronly," Arch Intern med, 1999;159:337-345.

Lacy et al., Drug Information Handbook, 1999-2000, Lexi-Comp, pp. 90-93.

Giaid et al, "Expression of Endothelin-1 in the Lungs of Patients with Pulmonary Hypertension," NEJM, vol. 328:1732-1739, No. 24, Jun. 17, 1993, 2 pages.

Giaid et al., "Reduced Expression of Endothelial Nitric Oxide Synthase in the Lungs of Patients with Pulmonary Hypertension," NEJM, vol. 333:214-221, No. 4, Jul. 27, 1995, 2 pages.

Office Action dated Sep. 17, 2009 in related U.S. Appl. No. 11/333,514, filed Jan. 17, 2006.

Office Action dated Sep. 10, 2009 in related U.S. Appl. No. 11/251,737, filed Oct. 17, 2005.

Office Action dated Oct. 29, 2008 in related U.S. Appl. No. 11/251,737, filed Oct. 17, 2005.

Office Action dated Aug. 6, 2008 in related U.S. Appl. No. 10/635,048, filed Aug. 4, 2003.

Office Action dated Sep. 8, 2008 in related U.S. Appl. No. 11/333,514, filed Jan. 17, 2006.

Office Action dated Sep. 29, 2009 in related U.S. Appl. No. 11/747,167, filed May 10, 2007.

Office Action dated Mar. 20, 2009 in related U.S. Appl. No. 11/333,514, filed Jan. 17, 2006.

Office Action dated Jan. 28, 2009 in related U.S. Appl. No. 11/348,142, filed Feb. 6, 2006.

Office Action dated May 12, 2008 in related U.S. Appl. No. 11/747,167, filed May 10, 2007.

Office Action dated Aug. 18, 2008 in related U.S. Appl. No. 11/747,167, filed May 10, 2007.

Office Action dated Feb. 10, 2009 in related U.S. Appl. No. 11/747,167, filed May 10, 2007.

Zhang et al., "Upregulation of Vascular Arginase in Hypertension Decreases Nitric Oxide-Mediated Dilation of Coronary Arterioles," Hypertension, 2004;44;935-943.

Taddei et al., "Role of Endothelin in the Control of Peripheral Vascular Tone in Human Hypertension," Heart Failure Reviews, 2001, 6, 277-285.

Office Action dated Apr. 10, 2009 in related U.S. Appl. No. 11/927,172, filed Oct. 29, 2007.

Office Action dated Jul. 9, 2009 in related U.S. Appl. No. 11/927,172, filed Oct. 29, 2007.

Office Action dated Sep. 2, 2010 in related U.S. Appl. No. 11/625,448, filed Jan. 22, 2007.

Office Action dated Dec. 9, 2009 in related U.S. Appl. No. 11/838,788, filed Aug. 14, 2007.

Office Action dated Jul. 13, 2009 in related U.S. Appl. No. 10/536,584, filed Apr. 7, 2006.

Office Action dated Feb. 25, 2010 in related U.S. Appl. No. 10/536,584, filed Apr. 7, 2006.

English Translation of French Patent 2,590M issued on Jun. 15, 1964, 11 pages.

* cited by examiner

THERAPEUTIC TREATMENT

This application is a continuation of U.S. patent application Ser. No. 11/333,514, filed on Jan. 17, 2006, which is a continuation-in-part application of PCT/BE2004/00101 filed on 8 Jul. 2004, published on Jan. 1, 2005 as WO2005004854, which claims priority from Belgium application No. BE 2003/0408 filed Jul. 15, 2003, the disclosure of each of the foregoing being incorporated herein by reference.

FIELD OF THE INVENTION

The present invention describes the use of betaine for the treatment and the prevention of arteritis. The present invention also describes an oral composition for the treatment of arteritis and in particular for the treatment of intermittent claudication, said composition comprising as a single active ingredient a therapeutically active amount of glycine betaine by unit dose. More particularly the invention describes a drug intended to treat a suffering patient of an intermittent claudication caused by peripheral circulatory disorders such as obliterating arteriosclerosis or Thromboangiitis obliterans.

PRINCIPLE OF THE INVENTION

Arteritis is an inflammation of the arteries. Anatomically, the inflammatory lesions can affect one or more vascular coats leading to pathologies such as endarteritis, mesarteritis, periarteritis or even the inflammation can affect the entire coats of an artery which is then termed panarteritis. Arteritis can be widespread to the entire organism, localized within a vascular territory (arteritis of the lower limbs) or even limited to only one vessel (the temporal artery in the disease of Horton) or to portions of a vessel (knotty periarteritis).

Theoretically there are two groups of arteritis: acute arteritis and chronic arteritis. In practice three large varieties of arteritis can be defined:
1. Infectious arteritis, either acute (rickettsioses) or subacute which are panarteritis;
2. Degenerative arteritis, which are especially endarteritis or mesarteritis, which affect elder subjects, are mainly caused by a sclerosis (arteriosclerosis, arteriolosclerosis) or by lipidic deposits (atheroma);
3. Crypto-genetics Arteritis (of unknown cause, allotted sometimes to immunological disorders), which are usually collagenoses (knotty periarteritis, acute disseminated erythematosus lupus, Wegener disease, Buerger disease, temporal arteritis, etc).

Anatomical complications caused by the arterial lesions, whatever is the cause are two:
The weakening of the arterial wall which is at the origin of distension or of an aneurism with it is at risk of rupture;
The thickening of the arterial wall which decreases the lumen of the vessel favouring thrombosis.

The arterial distension (aneurism) and thrombosis involve a bad vascularisation in the territories irrigated by these vessels which is a possible cause of atrophy and infarction. As it is seen thrombosis in this case is only one of the manifestations of arteritis which is as an upstream event. In this precise case also thrombosis is caused by mechanical forces (shear stress) involving platelet aggregation in consequence of their activation, the homocysteine not having any causative effect. Arteritis manifestation on the level of the lower limbs may cause intermittent claudication, a pain of the cramp type of the muscular masses of the calf, appearing with the effort (usually walking) and yielding at rest. The pain appears after a called distance covered perimeter of walk whose importance decreases when the disease worsens, rendering any walk then impossible.

When the pains persist even at rest, it is necessary to fear the appearance of gangrene, major complication of arteritis. The gangrene seems an initially purplish zone then wiring to black, which can extend quickly and require amputation. The diagnosis of arteritis is evoked in case of the cooling of a member, the reduction or even the abolition of the arterial beats, the reduction or the disappearance of the oscillations which one seeks with an oscillometer of Pachon. The arteriography is essential to specify the exact state of the arterial trunk. In front of any arteritis it is necessary to seek diabetes because arteritis is frequent in diabetic patients and become complicated readily by gangrene. Chronic obliterating arteriopathy is due to the formation of atheroma plaques within the arterial wall. The atheromatous deposit is an irreversible lesion which reaches the three layers of the arterial wall. This later (the arterial wall) sees its diameter decreasing gradually with the evolution of the disease, until inducing an ischemia of the territory irrigated by the artery. In fact, the arteriopathy of the lower limbs is a late manifestation of atherosclerosis: it is common that these patients also have atherosclerosis attacks of the coronary arteries, carotids and abdominal aorta. If the process originating the development of the atheroma plaque remains poorly understood, the factors of risk are well-known: tobacco, arterial hypertension, diabetes, hypercholesterolemia (increase in LDL/HDL ratio). Varices are also clinical manifestations of arteritis and are abnormal and permanent dilations of superficial veins. The insufficiency of the ostiale valve on the level of the saphenous vein crook (saphenous-femoral junction) plays an essential role in the development of the varices of the subjacent veins. The increase of the pressure in the superficial veins as the resulting blood stasis can be at the origin of trophic disorders. Venous claudication is also a manifestation of arteritis, just as is the Raynaud's Syndrome.

Intermittent claudication means symptoms in which two conditions follow each others and are repeated: the difficulty of continuous walk provoking discomfort and muscular pains of the lower limbs caused after the locomotion of a constant distance and the reduction of these symptoms or the possibility of again being able to be move without pain after a rest of several minutes. Arterial intermittent claudication corresponds to an ischemic pain following an effort of the lower limbs which is secondary to an obliterating chronic arteriopathy. The pain is related to a relative blood supply insufficiency of an additional metabolic request to a muscular group, said supply insufficiency leading to acidosis.

Arteritis also induces necroses on various tissues and organs.

The purpose of the invention is the therapeutic or pharmaceutical use of the glycine betaine of formula $(CH_3)_3N^+(CH_2)COO^-$ and its pharmaceutically acceptable salts in order to prevent and/or treat arteritis and the affections which they cause, in particular the various pathologies, manifestations and complications described in the present application.

In an aspect of the invention the lipidic betaines, the combinations and the formulations as described in PCT/IB 02/04923 of the inventor could be used.

In another particular aspect the use of a betaine in combination with stem cells is claimed.

In another general aspect of the invention a method of treatment combining the therapeutical uses of at least one or more betaine in combination with at least one or more stem cells is claimed. Accordingly, I claim the methods of treatment suitable in the various clinical settings, pathologies and therapies where stem cells can be used. Accordingly, the combined use of betaine can augment stem cells therapies effectiveness and/or augment host body acceptance of such stem cells and/or augment stem cells viability inside a host body and/or augment stem cells viability outside a host body and/or lessen at least one or more side effect associated to stem cells therapies. Betaine compounds can be administrated before, during, after and their combinations with at least one or more stem cells line according to different chronologies and/or different administrations paths.

The invention has particular aim the use of the glycine betaine as an active or pharmaceutical ingredient for the treatment and/or the prevention of degenerative arteritis. For example, there is remark that the glycine betaine was adapted to reduce or limit the rapidity of development of degeneration of degenerative(s) arteritis, even to stop or block the development of degeneration of degenerative(s) arteritis, or better even to provoke the remission at least partial of degeneration of degenerative(s) arteritis.

STATE OF THE ART

The treatments used currently for arteritis can be the vasodilators which are often insufficient. The oral anticoagulants such as warfarin delay the appearance of thromboses. The antibiotics suppress the infection of gangrene. Surgical treatment can be necessary in the event of non effectiveness of these treatments.

The medicament treatment is indicated in the absence of significant improvement of claudication after 6 months of standardized rehabilitation or for too old patients to profit from such medical management. But these drug treatments did not proved to be statistically effective to reduce, even limit the rapidity of degeneration of arteritis degenerative(s), and thus even less to stop or block the degeneration. In the particular case of intermittent claudication the drugs used are for example, the pentoxifylline which has the effect to improve the deformability of the red globules and by the way improve viscosity of blood, naftidrofuryl, aspirin, clopidogrel and cilostazol which has antiaggregant and vasodilating activities. These agents have shown a certain clinical effectiveness but their use remains related to considerable side effects. Low molecular weight Heparins, ticlopidine, clopidogrel and aspirin were also tested with variable results.

One knows various therapeutic uses of the betaine in particular those described in the following documents:

U.S. Pat. No. 6,008,221 and U.S. Pat. No. 6,127,370 describe a method of treatment of Alzheimer's disease where one combines a folic acid with a betaine in order to reduce rates of homocysteine. The method of treatment also describes the use of such combinations in order to reduce microvascular events possibly inducing neuro-degenerations. Intermittent claudication is described. In these applications one teaches the use of the betaine by oral route, but in extremely small quantity, in particular in claim 12 where the daily amount of betaine proposed varies between 0.1 to 100 mg, such amount being much too weak to be able to produce any unspecified therapeutic effect.

WO 00/25764 describes a combination comprising a methyl donor, a vitamin and a bioflavonoid in order to reduce the homocysteine and in particular the diseases associated with the hyper homocysteinemia. The authors when listing the diseases associated with hyperhomocysteinemia refer to Intermittent Claudication. But the authors do not provide any specific example concerning Intermittent Claudication, neither any scientific basement clearly establishing a link between this pathology and hyperhomocysteinemia. This document only teaches that the intended mixture is destined to lower homocysteine and in any case such document does not teach that the single ingredient betaine can improve the Initial Claudication Distance, nor the Maximal Walking Distance, nor the social functioning of the patients. In fact homocysteine has no effect on such variables. For instance licensed drugs such as pentoxifylline or cilostazoi have no incidence on Hcy in clinical setting showing by the way that ameliorating the clinical outcome or walking ability is independent of homocysteine. Although cited in different articles relating to IC, homocysteine role remains speculative or controversial in such pathology. Although supplementing the diet with B vitamins and folate usually lowers serum homocysteine concentrations no controlled trials demonstrate that reducing serum homocysteine concentration is beneficial in patients with PAD (peripheral artery disease) or PAOD (peripheral artery occlusive disease). American Academy of Family Physicians, Daniela C. & al, February 1, (http://www.aafp.org/afp/20040201/525.html)

Moreover WO 00/25764 describes in its single example an oral composition intended for a single catch, the aforementioned composition containing 600 mg of betaine, 0.5 mg of salt calcium of acid L-5-Methyl will tetra hydro-folic and 500 mg of Isoquercetine. The use of bioflavonoides as of vitamins in addition to the betaine does not bring anything to the therapeutic point of view in the treatment intermittent claudication, moreover being a composition intended for a single use the quantity of betaine used for each single catch does not make possible to reach therapeutic concentrations of betaine necessary within sight of the weak absolute bioavaibility by oral way of the latter. The compounds claimed in this document by the contribution of non-effective ingredients in intermittent claudication, could compromise the effectiveness of the betaine in this pathology and do not provide effectives amounts of betaine necessary for a therapeutic effect nor do not allow an optimal and/or effective medication.

WO 00/25764 does not teach, nor suggests that betaine administration as a single active ingredient can improve the walking performance of patients affected by peripheral arterial disease or by intermittent claudication.

WO 00/25764 does not teach, nor suggests a method of treatment to improve the walking performance of patients affected by peripheral arterial diseases and/or by intermittent claudication said method consisting in administering a therapeutically effective amount of a betaine as a single active ingredient and/or in combination with one or more compounds selected from the group consisting of Cilostazol, pentoxifylline, prostaglandins naftidrofuryl, aspirin, clopidogrel, levocarnitine, propionyl levocarnitine, and mixtures thereof.

WO 00/25764 does not teach a method to improve the pain free distance of patients affected by peripheral arterial diseases and/or by intermittent claudication said method consisting in administering a therapeutically effective amount of a betaine as a single active ingredient and/or in combination with one or more compounds selected from the group consisting of Cilostazol, pentoxifyiline, prostaglandins naftidrofuryl, aspirin, clopidogrel, levocarnitine, propionyl levocarnitine, and mixtures thereof.

WO 00/25764 does not teach a method to improve the pain free distance and/or the maximal walking distance of patients affected by peripheral arterial diseases and/or by intermittent claudication trouble such as Leriche-Fontaine stage I, stage II, stage III & stage IV PAD.

WO 00/25764 does not teach a method to improve the maximal walking distance of patients affected by peripheral arterial diseases and/or by intermittent claudication said method consisting in administering a therapeutically effective amount of a betaine as a single active ingredient and/or in combination with one or more compounds selected from the group consisting of Cilostazol, pentoxifylline, prostaglandins naftidrofuryl, aspirin, clopidogrel, levocarnitine, propionyl levocarnitine, and mixtures thereof.

WO 00/25764 does not teach a method to improve the sense of well being and the functional social status of patients affected by peripheral arterial diseases and/or by intermittent claudication said method consisting in administering a therapeutically effective amount of a betaine as a single active ingredient and/or in combination with one or more compounds selected from the group consisting of Cilostazol, pentoxifylline, prostaglandins naftidrofuryl, aspirin, clopidogrel, levocarnitine, propionyl levocarnitine, and mixtures thereof.

In a particular embodiment the invention claim also the use of a betaine, preferably glycine betaine of formula $(CH3)_3N^+(CH2)COO^-$ and its pharmaceutically acceptable salts in order to prevent and/or treat peripheral occlusive diseases and/or peripheral arterial diseases, and/or vascular diseases and/or cardiac diseases in patients with normal homocysteine levels. According to American Heart Association (Malinow & al, Circulation. 1999; 99:178-182) normal levels of fasting plasma homocysteine are considered to be between 5 and 15 µmol/L. Moderate, intermediate, and severe hyperhomocysteinemia refer to concentrations between 16 and 30, between 31 and 100, and >100 µmol/L, respectively.

WO 00/51596 and WO 02/062322 describe the use of the antithrombotic betaine like agent, only or in combination with other molecules. Thrombosis being a possible consequence of arteritis and is downstream from those.

These documents thus do not teach that the betaine would make it possible to treat arteritis, in particular degenerative arteritis. None of these documents describes the use of the betaine in order to prevent and/or treat arteritis. Surprisingly the inventor discovered the remarkable properties of the glycine betaine to treat and/or prevent arteritis as well as the pathological affections related to those pathologies.

The inventor also found that betaine administration can treat and/or ameliorate and/or improve one or more of the following: Haemodynamic measurement as ankle/brachial index (ABI), walking performance, pain free distance, maximal walking distance, sense of well being and the functional social status of patients affected by peripheral arterial diseases and/or by intermittent claudication.

In a preferred embodiment, walking performance measured as pain free distance (ICD) and maximal or absolute walking distance (ACD) can be assessed using one or more treadmill tests. It is advisable to use the same test both before and after administration of the therapeutic agent hereof in order to obtain a valid assessment.

In a preferred embodiment, walking performance measured as pain free distance (ICD) and maximal or absolute walking distance (ACD) can be assessed using one or more treadmill tests standardized to a constant 12% grade inclination and at a constant speed of 3.2 km/hour.

In a preferred embodiment sense of well being and/or the functional social status can be assessed using one or more validated questionnaires.

In a preferred embodiment sense of well being and/or the functional social status can be assessed using one or more validated questionnaires such as Quality-of-life questionnaire scores in WIQ (Walking impairment Questionnaire) and/or MOS SF-36 (Medical Outcomes Study questionnaire).

In a particular embodiment the methods of the invention are claimed to have less side effects than the existing treatments and/or methods.

In another particular embodiment the methods of the invention are claimed to lessen the side effects of existing treatments and/or to improve the effectiveness of such existing treatments for peripheral arterial diseases and/or intermittent claudication.

Pain free walking distance stands for the distance walked by a patient suffering from peripheral arterial disease and/or intermittent claudication before the onset or the appearance of pain in its lower limbs.

Absolute or maximum claudication distance (ACD) is the absolute or the maximal distance walked by the patient before the first to occur of pain or cramps in his/her lower limbs force him/her to stop walking.

Initial claudication distance (ICD) is the distance when the patient first reported the onset of the first to occur of pain or cramps in his/her lower limbs, i.e., the onset of claudication symptoms (pain-free walking distance).

The definitions of the terms ACD & ICD are those given by the FDA in the approval label for cilostazol (Pletal®) (see Effectiveness at http://www.fda.gov/cder/news/cilostazol/approval.htm), the disclosure of which is incorporated herein by reference.

PAOD is classified using the Fontaine Staging System. The initial claudication distance (distance at which the patient first experiences pain with exertion) and the absolute claudication distance (distance at which the patient can no longer ambulate) are usually constant. With advancing disease or acute ischemia, patients may complain of a sudden decrease in the initial claudication distance, disabling claudication, or rest pain, or on examination may be found to have ulceration or tissue loss.

The ankle-brachial index is an effective screening tool. The tools required to obtain an ankle-brachial index include a blood pressure cuff and a continuous wave Doppler. Blood pressure is measured in both upper extremities, and the highest systolic reading—the first return of Doppler sound as the cuff is deflated—is recorded. The ankle systolic pressure is similarly measured using the dorsalis pedis or posterior tibial arteries. The ankle-brachial index is calculated by dividing the ankle pressure (the higher of the posterior tibial artery pressures) by the brachial systolic pressure (the higher of the two arm pressures). An ankle-brachial index below 0.95 at rest or following exercise is considered abnormal. American Academy of Family Physicians, Theresa L. et al, (http://www.aafp.org/afp/20000215/1027.html).

Patients with peripheral arterial disease (PAD) report profound limitations in all domains of quality of life that are worse than those for patients with chronic pulmonary disease and moderate to severe heart failure.

Claudication and PAD had a greater impact on women than on men and may result from the higher prevalence of mood disturbance and bodily pain reported by women. In a particular embodiment the present invention provides methods and treatments based on the therapeutic or pharmaceutical uses of betaine of formula $(CH3)_3N^+(CH2)COO^-$ and its pharmaceutically acceptable salts, in order to ameliorate the quality of life of patients, their sense of well being and to lessen the deficits related to such vascular pathologies.

The invention relates to a method for increasing walking distance in a patient suffering of peripheral arterial disease and/or intermittent claudication, said method comprising administering to said patient a therapeutically effective amount of at least one therapeutically active compound selected from the group consisting of $(CH_3)_3N^+(CH_2)COO^-$, pharmaceutically pharmaceutically active salts thereof and mixtures thereof.

Advantageously, the method is adapted for increasing the walking distance of said patient by at least 10%, preferably at least 20%, most preferably at least 30% with respect to the walking distance (average walking distance) of said patient before his treatment, whereby said walking distance is increased by at least 20 meters, advantageously at least 40 meters, preferably at least 60 meters, most preferably at least 100 meters. For normalizing the increase of walking distance, the walking distance is determined by assessing the patient by a constant-load treadmill testing at a 12% grade inclination and a speed of 3.2 km/h. Such test underestimates the therapeutic effects of a study medication. (Skinner J S, Strandness D E Jr. Exercise and intermittent claudication, I: effect of repetition and intensity of exercise. Circulation. 1967; 36: 15-22)

The invention relates also to:

A method for increasing the walking distance without pain in muscles of lower limbs in a patient suffering from peripheral arterial occlusive disease and/or intermittent claudication, said method comprising administering to said patient a therapeutically effective amount of at least one therapeutically active compound selected from the group consisting of $(CH_3)_3N^+(CH_2)COO^-$, pharmaceutically active salts thereof and mixtures thereof.

A method for increasing the initial claudication distance in a patient suffering from peripheral arterial diseases and/or intermittent claudication, said method comprising administering to said patient, as therapeutically active agent for increasing the initial claudication distance, a therapeutically effective amount of at least one therapeutically active compound selected from the group consisting of $(CH_3)_3N^+(CH_2)COO^-$, pharmaceutically active salts thereof and mixtures thereof.

A method for increasing the absolute claudication distance in a patient suffering from peripheral arterial diseases and/or intermittent claudication, said method comprising administering to said patient, as therapeutically active agent for increasing the absolute claudication distance, a therapeutically effective amount of at least one therapeutically active compound selected from the group consisting of $(CH_3)_3N^+(CH_2)COO^-$, pharmaceutically active salts thereof and mixtures thereof.

A method for increasing ACD and/or ICD (walking distances) and for preventing stroke in a patient suffering of peripheral arterial disease and/or intermittent claudication and at risk from suffering from thrombosis, said method comprising administering to said patient a therapeutically effective amount of at least one therapeutically active compound selected from the group consisting of $(CH_3)_3N^+(CH_2)COO^-$ pharmaceutically active salts thereof and mixtures thereof.

A method for increasing ACD and/or ICD (walking distances) and for preventing headache in a patient suffering of peripheral arterial disease and/or intermittent claudication and at risk from suffering headache due to an other treatment than a betaine for his peripheral artery occlusive disease, said method comprising administering to said patient a therapeutically effective amount of at least one therapeutically active compound selected from the group consisting of $(CH_3)_3N^+(CH_2)COO^-$, pharmaceutically active salts thereof and mixtures thereof.

A method for increasing ACD and/or ICD (walking distances) in a patient suffering of peripheral arterial disease and/or intermittent claudication, said method comprising administering to said patient a therapeutically effective amount of a first active agent effective for treating peripheral artery occlusive disease and a therapeutically effective amount of a second active agent different from the first active agent, whereby said second effective agent is selected from the group consisting of $(CH_3)_3N^+(CH_2)COO^-$, pharmaceutically active salts thereof and mixtures thereof. In said method, the first active agent is advantageously Cilostazol, pentoxifylline, prostaglandins, naftidrofuryl, aspirin, clopidogrel, levocarnitine, propionyl levocarnitine, and mixtures thereof, preferably Cilostazol.

A method for increasing ACD and/or ICD (walking distances) in a patient suffering of peripheral arterial disease and/or intermittent claudication, said method comprising administering to said patient a therapeutically effective amount of a first active agent effective for treating peripheral artery occlusive disease, said first active agent having at least one side effect selected from the group consisting of thrombosis, stroke, palpitation, headache, loose stool samples, soft stool samples, and a therapeutically effective amount of a second active agent different from the first active agent for preventing said at least one side effect of the first active agent, whereby said second effective agent is selected from the group consisting of $(CH_3)_3N^+(CH_2)COO^-$, pharmaceutically active salts thereof and mixtures thereof. In said method, the first active agent is advantageously Cilostazol, pentoxifylline, prostaglandins, naftidrofuryl, aspirin, ciopidogrel, levocarnitine, propionyl levocarnitine, and mixtures thereof, preferably Cilostazol, A method for increasing ACD and/or ICD (walking distances) in a patient suffering of peripheral arterial disease and/or intermittent claudication, said method comprising administering to said patient a therapeutically effective amount of a first active agent effective for treating peripheral artery occlusive disease for increasing the walking distance pain in muscles of lower limbs, and a therapeutically effective amount of a second active agent different from the first active agent, whereby said second effective agent is selected from the group consisting of $(CH_3)_3N^+(CH_2)COO^-$, pharmaceutically active salts thereof and mixtures thereof, said second agent improving at least one effect selected from the group consisting of the walking distance achieved by the first active agent taken alone, the time onset for achieving a 10% improvement of the walking distance with respect to the walking distance achieved without pain by the patient not treated for his peripheral artery occlusive disease, the time onset for achieving a 20 m improvement of the walking distance with respect to the walking distance achieved without pain by the patient not treated for his peripheral artery occlusive disease, and combinations thereof. In said method, the first active agent is advantageously Cilostazol, pentoxifylline, prostaglandins, naftidrofuryl, aspirin, clopidogrel, levocarnitine, propionyl levocarnitine, and mixtures thereof, preferably Cilostazol.

A method for increasing at least one walking distance selected from the group consisting of absolute claudication distance and initial claudication distance, (especially both distances ACD and ICD), in a patient suffering of peripheral arterial disease and/or intermittent claudication, said method comprising administering to said patient a therapeutically effective amount of a first active agent effective for treating peripheral artery occlusive disease for increasing at least one walking distance selected from the group consisting of absolute claudication distance and initial claudication distance, (especially both distances ACD and ICD), and a therapeutically effective amount of a second active agent different from the first active agent, whereby said second effective agent is selected from the group consisting of $(CH_3)_3N^+(CH_2)COO^-$, pharmaceutically active salts thereof and mixtures thereof, said second agent improving at least one effect selected from the group consisting of the absolute walking distance achieved by the first active agent taken alone, the initial claudication distance achieved by the first active agent taken alone, the time onset for achieving a 10% improvement of the at least one walking distance selected from the group consisting of absolute claudication distance and initial claudication distance, (especially both distances ACD and ICD) with respect to the walking distance achieved without pain by the patient not treated for his peripheral artery occlusive disease, the time onset for achieving a 20 m improvement of the walking distance with respect to the walking distance achieved without pain by the patient not treated for his peripheral artery occlusive disease, and combinations thereof. In said method, the first active agent is advantageously Cilostazol, pentoxifylline, prostaglandins, naftidrofuryl, aspirin, clopidogrel, levocarnitine, propionyl levocarnitine, and mixtures thereof, preferably Cilostazol.

In any methods of the invention, a therapeutically effective amount of at least one therapeutically active compound selected from the group consisting of $(CH_3)_3N^+(CH_2)COO^-$, pharmaceutically active salts thereof and mixtures thereof is preferably daily administered to said patient for at least 4 weeks, advantageously for at least 3 months.

Most preferably, an effective therapeutic amount of at least one therapeutically active compound selected from the group consisting of $(CH_3)_3N^+(CH_2)COO^-$, pharmaceutically active salts thereof and mixtures thereof is orally administered to said patient.

According to a preferred embodiment of any of said methods, the therapeutically active compound selected from the group consisting of $(CH_3)_3N^+(CH_2)COO^-$, pharmaceutically active salts thereof and mixtures thereof is administered to said patient with a dosage form selected from the group consisting of once daily administration forms and the twice daily administration forms.

Other details or characteristics of methods of the invention are:
  the therapeutically active compound selected from the group consisting of $(CH_3)_3N^+(CH_2)COO^-$, pharmaceutically active salts thereof and mixtures thereof is administered to said patient with an extended release dosage form.
  at least 1000 mg of the therapeutically active compound selected from the group consisting of $(CH_3)_3N^+(CH_2)COO^-$, pharmaceutically active salts thereof and mixtures thereof (for example from 2 g to 15 g, such as 3 g, 4 g, 5 g, 6 g, 8 g, 10 g) is daily administered to said patient as an immediate release dosage form.
  at least 250 mg (advantageously from 500 mg to 6000 mg, preferably from 750 mg to 3000 mg) of the therapeutically active compound selected from the group consisting of $(CH_3)_3N^+(CH_2)COO^-$, pharmaceutically active salts thereof and mixtures thereof is daily administered to said patient as an extended release dosage form,
  from 250 mg to 3000 mg of the therapeutically active compound selected from the group consisting of $(CH_3)_3N^+(CH_2)COO^-$, pharmaceutically active salts thereof and mixtures thereof is daily administered to said patient as an extended release dosage form.
  from 250 mg to 1000 mg of the therapeutically active compound selected from the group consisting of $(CH_3)_3N^+(CH_2)COO^-$, pharmaceutically active salts thereof and mixtures thereof is daily administered to said patient as an extended release dosage form.
  at least 250 mg of the therapeutically active compound selected from the group consisting of $(CH_3)_3N^+(CH_2)COO^-$, pharmaceutically active salts thereof and mixtures thereof is daily administered to said patient as an extended release dosage form, while at least 250 mg of the therapeutically active compound selected from the group consisting of $(CH_3)_3N^+(CH_2)COO^-$, pharmaceutically active salts thereof and mixtures thereof is daily administered to said patient as an immediate release dosage form. Advantageously, at least one unit dosage form comprising an immediate release dosage portion of at least 250 mg of the therapeutically active compound selected from the group consisting of $(CH_3)_3N^+(CH_2)COO^-$, pharmaceutically active salts thereof and mixtures thereof and an extended release dosage portion of at least 250 mg of the therapeutically active compound selected from the group consisting of $(CH_3)_3N^+(CH_2)COO^-$, pharmaceutically active salts thereof and mixtures thereof is daily administered to said patient.

The invention further relates to a pharmaceutical combination for increasing at least one walking distance selected from the group consisting of absolute claudication distance and initial claudication distance, (especially both distances ACD and ICD), in a patient suffering of peripheral arterial disease and/or intermittent claudication, said combination comprising administering to said patient a therapeutically effective amount of a first active agent effective for treating peripheral artery occlusive disease and a therapeutically effective amount of a second active agent different from the first active agent, whereby said second effective agent is selected from the group consisting of $(CH_3)_3N^+(CH_2)COO^-$, pharmaceutically active salts thereof and mixtures thereof.

Advantageously, the weight ration first active agent/second active agent is comprised between 1:100 and 100:1, such as between 1:50 and 50:1, advantageously between 1:40 and 20:1.

Preferably, the weight ration first active agent/second active agent is comprised between 1:40 and 1:1, most preferably between 1:30 and 1:3, especially between 1:25 and 1:5.

According to an advantageous embodiment, the second active agent is at least partly in an extended release form.

According to another embodiment, the first active agent is at least partly in an immediate release form.

For example, the two active agents present in the combination are present in two distinct compositions which are placed in a capsule or in a tablet or tableted together with one or more tabletting agent. The second active agent is for example contained in a core, tablet or granules provided with a coating layer containing the first active agent. Advantageously, one or more barrier layer and/or controlled release layers are provided between the core, granule, tablet and the layer containing the first active agent. According to another embodiment, the first active agent is in the form of coated or uncoated granules, micro-granules, tablets, matrix, while the second active agent is also in the form of coated or uncoated granules, tablets, matrix, etc., said forms being exempt from the first active agent. The said distinct forms containing the first active agent and the forms containing the second active agent are placed in one capsule or are tableted together for forming a single dosage form.

The two active agents to be administered substantially simultaneously can also have the form of two distinct solid or substantially solid dosage forms, which are placed in one single blister support.

Advantageously, the first active agent is cilostazol, pentoxifylline, prostaglandins, naftidrofuryl, aspirin, ciopidogrel, levocarnitine, propionyl levocarnitine, and mixtures thereof. Cilostazol is preferred.

For example, the combination comprises from 10 to 200 mg of first active agent and from 250 mg to 3000 mg of second active agent.

The combination is advantageously in the form of unitary dosage form.

Most preferably, the combination is an oral formulation.

The invention has as an aim the use of the glycine betaine as a therapeutically active principle for the treatment and/or the prevention of arteritis or for obtaining a drug intended for the treatment of one or more arteritis.

The invention also has as an aim the use of the glycine betaine as a therapeutically active principle for the treatment of arteritis or obtaining a drug intended for the treatment of degenerative arteritis, in particular for obtaining a drug intended for the prevention of at least degenerative arteritis, even for obtaining a drug intended to reduce or limit the speed of development of degeneration of arteritis degenerative(s), or better for obtaining a drug intended to stop or block the development of degeneration of degenerative(s) arteritis and/or for obtaining a drug intended for the remission at least partial of degeneration of degenerative(s) arteritis, According to an embodiment, the invention has as an aim the use of the glycine betaine for the preparation of an oral therapeutic combination for the treatment of arteritis and/or intermittent claudication, the aforementioned combination including/understanding like single active ingredient at least 500 mg (advantageously at least 1000 mg, in particular 2000 to 10000, preferably from 3000 to 7000 mg of glycine betaine in a form with immediate release) of glycine betaine by unit dose and/or at least 500 mg of a mixture of glycine betaine and aspirin like active ingredients and/or active basic interconnection of glycine betaine and aspirin. Advantageously, the composition or unit combination with said usage contains at least 1000 mg of glycine betaine in a form with immediate release, in particular 2000 to 10000, preferably from 3000 to 7000. Preferably, the composition or unit combination with spoken usage contains at least 250 mg of glycine betaine in a form with controlled release, more specifically at least 250 mg of glycine betaine in a form with controlled release and at least 250 mg of glycine betaine in a form with immediate release. In a particular aspect of the invention, a betaine can also be associated an agent anti-cholesterol, such a statin, in order to treat the pathologies described in the present application. In an optional way a pharmaceutical composition combining aspirin/betaine/agent anti-cholesterol is also asserted.

The invention further claims:

a method of treatment of a suffering patient of arteritis, in which one manages to that the patient a quantity therapeutically active glycine betaine for the treatment of arteritis.

a method to prevent at a patient the appearance of arteritis, in which one manages to that the patient a quantity therapeutically active glycine betaine to prevent the aforementioned arteritis.

a method of treatment of a suffering patient of arteritis, in which one manages to that the patient a quantity therapeutically active glycine betaine for the treatment of arteritis degenerative(s).

a method of treatment of a suffering patient of arteritis, in which one manages to that the patient a quantity therapeutically active of glycine betaine for the prevention of at least degenerative arteritis.

a method of treatment of a suffering patient of arteritis, in which one manages to that the patient a quantity therapeutically active of glycine betaine to reduce or limit the speed of development of degeneration of arteritis degenerative(s).

a method of treatment of a suffering patient of arteritis, in which one manages to that the patient a quantity therapeutically active of glycine betaine to stop or block the development of degeneration of arteritis degenerative(s).

a method of treatment of a suffering patient of arteritis, in which one manages to that the patient a quantity therapeutically active of glycine betaine for the remission at least partial of degeneration of arteritis degenerative(s).

In these methods, one manages advantageously (in particular by oral way) with the patient in manner daily at least 500 mg (advantageously at least 1000 mg, in particular 2000 to 10000, preferably from 3000 to 7000 mg of glycine betaine in a form with immediate release) of glycine betaine, advantageously in the form of a unit dose and/or of an amount with single catch daily, and/or of a mixture of glycine betaine and aspirin like active ingredients and/or active basic interconnection of glycine betaine and aspirin. In particular, one manages with the patient in manner daily at least 1000 mg (advantageously at least 1500 mg, in particular 2000 to 10000, preferably from 3000 to 7000 mg of glycine betaine in a form with immediate release) of glycine betaine in a form with immediate release. More specifically, one manages with the patient in manner daily at least 250 mg of glycine betaine in a form with controlled release. For example, one manages with the patient in manner daily at least 250 mg, in particular at least 750 mg of glycine betaine in a form with controlled release and at least 250 mg of glycine betaine in a form with immediate release. The present invention also asserts the use of at least a betaine of formula $(CH3)_3N^+(CH_2)COO^-$ and its pharmaceutically acceptable salts in order to prevent, to relieve and/or to treat Raynaud's Syndrome as well as the dependent physiopathological attacks of this affection. In a particular aspect, the present invention also asserts the use of at least a betaine of formula $(CH3)_3N^+(CH_2)COO^-$ and its pharmaceutically acceptable salts in order to prevent, to relieve and/or to treat the disease of Burger as well as the dependent physiopathological attacks has this affection. In another particular aspect, the present invention also asserts the use of at least a betaine of formula $(CH3)_3N^+(CH_2)COO^-$ and its pharmaceutically acceptable salts in order to prevent, to relieve and/or to treat the varices as well as the dependent physiopathological attacks has this affection. In another particular aspect, the present invention also asserts the use of at least a betaine of formula $(CH3)_3N^+(CH_2)COO^-$ and its pharmaceutically acceptable salts in order to prevent, to relieve and/or deal with the problems of circulation and microcirculation related to the heavy legs as well as the dependent physiopathological attacks this affection or state has. In another particular aspect, the present invention also asserts the use of at least a betaine of formula $(CH3)_3N^+(CH_2)COO^-$ and its pharmaceutically acceptable salts in order to prevent, to relieve and/or to treat temporal arteritis, temporal arteritis gigantic-cellular, the disease of Horton as well as the dependent physiopathological attacks has these affections or states such as the cephalgias, the intermittent claudication of the jaw at the time of the efforts of chewing, lingual pains, sensitivity of the scalp, blindness as well as the indurations of the temporal arteries. In another particular aspect, the present invention also asserts the use of at least a betaine of formula $(CH3)_3N^+(CH_2)COO^-$ and its pharmaceutically acceptable salts in order to prevent, to relieve and/or treat an oedema of the posterior pole of the eye, the functional loss of the vision, the occlusion of the central artery of the retina as well as retinal ischemia. In another particular aspect, the present invention also asserts the use of at least a betaine of formula $(CH3)_3N^+(CH_2)COO^-$ and its pharmaceutically acceptable salts in order to prevent, to relieve and/or treat the dependent disorders a sedimentation test accelerated. In another particular aspect, the present invention also asserts the use of at least a betaine of formula $(CH3)_3N^+(CH_2)COO^-$ and its pharmaceutically acceptable salts in order to prevent, to relieve and/or treat the disorders related to the pains of inflammatory origin as in the disease of Horton. In another particular aspect, the present invention also asserts the use of at least a betaine of formula $(CH3)_3N^+(CH_2)COO^-$ and its pharmaceutically acceptable salts in order to prevent, to relieve and/or treat the disorders related to the male impotence as well as the genital disorders of arterial origin being able to occur in the event of vascular obstruction making erection, difficult In another particular aspect, the present invention also asserts the use of at least a betaine of formula $(CH3)_3N^+(CH_2)COO^-$ and its pharmaceutically acceptable salts in order to prevent, to relieve and/or treat the disorders related to the male impotence as well as the disorders related to erectile dysfunctions.

The invention relates to a method for treating a human suffering from various diseases or troubles caused by one or more various diseases and/or for treating a human at risk of suffering from various diseases or troubles caused by one or more various disease, in which an effective therapeutic amount of at least one therapeutically active compound selected from the group consisting of $(CH_3)_3N^+(CH_2)COO^-$, pharmaceutically active salts thereof and mixtures thereof is administered to said patient.

Advantageously, the invention relates to:

a method for treating a human suffering from the disease of Horton, in which an effective therapeutic amount of at least one therapeutically active compound selected from the group consisting of $(CH_3)_3N^+(CH_2)COO^-$, pharmaceutically active salts thereof and mixtures thereof is administered to said patient, and/or A method for treating a human at risk of suffering from the disease of Horton, in which an effective therapeutic amount of at least one therapeutically active compound selected from the group consisting of $(CH_3)_3N^+(CH_2)COO^-$, pharmaceutically active salts thereof and mixtures thereof is administered to said patient, and/or a method for treating at least one trouble associated to the disease of Horton in a human suffering from the disease of Horton, in which an effective therapeutic amount of at least one therapeutically active compound selected from the group consisting of $(CH_3)_3N^+(CH_2)COO^-$, pharmaceutically active salts thereof and mixtures thereof is administered to said patient, and/or a method for treating a human suffering from at least one trouble selected from the group consisting of varices, blood flow disturbances due to varices and combinations thereof, in which an effective therapeutic amount of at least one therapeutically active compound selected from the group consisting of $(CH_3)_3N^+(CH_2)COO^-$, pharmaceutically active salts thereof and mixtures thereof is administered to said patient, and/or a method for treating a human at risk of suffering from at least one trouble selected from the group consisting of varices, blood flow disturbances due to varices and combinations thereof, in which an effective therapeutic amount of at least one therapeutically active compound selected from the group consisting of $(CH_3)_3N^+(CH_2)COO^-$, pharmaceutically active salts thereof and mixtures thereof is administered to said patient, and/or a method for treating a human suffering from at least one trouble selected from the group consisting of oedemas, blood flow disturbances due to oedemas and combinations thereof, in which an effective therapeutic amount of at least one therapeutically active compound selected from the group consisting of $(CH_3)_3N^+(CH_2)COO^-$, pharmaceutically active salts thereof and mixtures thereof is administered to said patient, and/or a method for treating a human at risk of suffering from at least one trouble selected from the group consisting of oedemas, blood flow disturbances due to oedemas and combinations thereof, in which an effective therapeutic amount of at least one therapeutically active compound selected from the group consisting of $(CH_3)_3N^+(CH_2)COO^-$, pharmaceutically active salts thereof and mixtures thereof is administered to said patient, and/or a method for treating a human suffering from heavy leg and/or leg swelling and/or leg oedema and/or ankle swelling and/or ankle oedema, in which an effective therapeutic amount of at least one therapeutically active compound selected from the group consisting of $(CH_3)_3N^+(CH_2)COO^-$, pharmaceutically active salts thereof and mixtures thereof is administered to said patient, and/or a method for treating a human at risk of suffering from heavy leg and/or leg swelling and/or leg oedema and/or ankle swelling and/or ankle oedema, in which an effective therapeutic amount of at least one therapeutically active compound selected from the group consisting of $(CH_3)_3N^+(CH_2)COO^-$, pharmaceutically active salts thereof and mixtures thereof is administered to said patient, and/or a method for treating a human suffering from at least one disease selected from the group consisting of Raynaud's disease, Burger's disease and combination thereof, in which an effective therapeutic amount of at least one therapeutically active compound selected from the group consisting of $(CH_3)_3 N^+(CH_2)COO^-$, pharmaceutically active salts thereof and mixtures thereof is administered to said patient, and/or a method for treating a human at risk of suffering from at least one disease selected from the group consisting of Raynaud's disease, Burger's disease and combinations thereof, in which an effective therapeutic amount of at least one therapeutically active compound selected from the group consisting of $(CH_3)_3N^+(CH_2)COO^-$, pharmaceutically active salts thereof and mixtures thereof is administered to said patient, and/or a method for treating a human suffering from at least one trouble selected from the group consisting of intermittent claudication, erectile dysfunctions, retinal ischemia, occlusive central artery troubles, vision function losses and combinations thereof, in which an effective therapeutic amount of at least one therapeutically active compound selected from the group consisting of $(CH_3)_3N^+(CH_2)COO^-$, pharmaceutically active salts thereof and mixtures thereof is administered to said patient, and/or a method for treating a human at risk of suffering from at least one trouble selected from the group consisting of intermittent claudication, erectile dysfunctions, retinal ischemia, occlusive central artery troubles, vision function losses and combinations thereof, in which an effective therapeutic amount of at least one therapeutically active compound selected from the group consisting of $(CH_3)_3N^+(CH_2)COO^-$, pharmaceutically active salts thereof and mixtures thereof is administered to said patient, and/or a method for treating a human suffering from at least two different troubles (such as at least three, four or five or even more) selected from the group consisting of trouble of Horton, arteritis, varices, Raynaud's disease, Burger's disease, heavy leg and/or leg swelling and/or leg oedema and/or ankle swelling and/or ankle oedema, claudication, vision function losses, occlusive central artery, retinal ischemia, erectile dysfunction, temporal gigantic cell trouble, oedemas, blood flow disturbances due to oedemas and combinations thereof, in which an effective therapeutic amount of at least one therapeutically active compound selected from the group consisting of $(CH_3)_3N^+(CH_2)COO^-$, pharmaceutically active salts thereof and mixtures thereof is administered to said patient In another particular aspect, the present invention also claims the use of at least a betaine of formula $(CH3)_3N^+(CH_2)COO^-$ and its pharmaceutically acceptable salts in order to prevent, to relieve and/or treat the disorders related to the vasoconstriction of the circulatory system. Although the homocysteine does not have any causative effect in the expression of arteritis its worsening role in the vascular disease is now mentioned and in a particular aspect, the present invention also asserts the use of at least a betaine of formula $(CH_3)_3N^+(CH_2)COO^-$, and its pharmaceutically acceptable salts in order to treat arteritis while standardizing and/or lowering the plasmatic rates of homocysteine at a suffering patient of hyper homocysteinemia. The arteritis term of the lower limbs indicates in fact an obstructive chronic arteriopathy. This term gathers the lesions of the arterial wall whose evolution is the contracting or stenosis arterial gauge. The lower limbs are often reached by this arterial contracting which causes pains at the time of walk and can evolve until gangrene and amputation.

In a particular embodiment the invention claim also the use of a betaine, preferably glycine betaine of formula $(CH3)_3N^+(CH_2)COO^-$ and its pharmaceutically acceptable salts in order to prevent and/or treat varicose veins. Varicose veins are the largest ropey veins seen in the legs and spider veins are the smaller, often red or blue colored, veins. Varicose veins occur when the vein is not functioning correctly to help bring blood back up towards the heart. The walls of the veins are thinner, much less elastic and weaker then the walls of arteries. The veins start to enlarge most often in response to pressure. The pressure is typically from the forces of gravity, the body weight and the column of venous blood that has not yet finished its trip back to the heart. As a varicose vein enlarges it will contain larger volumes of blood, thus putting greater pressure on the valve below. If the pressure becomes severe enough to exceed the strength of the valve, then the varicosity enlarges further, thus putting even more pressure on the next valve it encounters, as the condition continues to worsen. The effects of gravity, body weight and the "uphill journey" are the primary reasons varicose veins occur almost exclusively in the legs and may be present in either one or both legs. The betaines of the invention, preferably glycine betaine of formula $(CH3)_3N^+(CH_2)COO^-$ and its pharmaceutically acceptable salts are thus claimed to be therapeutic in such pathologies as in their symptoms.

In a particular embodiment the invention claim also the use of a betaine, preferably glycine betaine of formula $(CH3)_3N^+(CH_2)COO^-$ and its pharmaceutically acceptable salts in order to prevent and/or treat spider veins. Spider veins are the thread-like colored veins most often seen on the surface of the skin. They are most often not as painful as enlarged varicose veins but they are still liable to bleed and worsen without treatment. Spider veins occur most commonly in the legs but are often seen in the face and elsewhere. These spider veins, medically referred to as telangectasias, will not worsen to the point where they will ever become the large bulging varicose veins. The betaines of the invention, preferably glycine betaine of formula $(CH3)_3N^+(CH_2)COO^-$ and its pharmaceutically acceptable salts in is thus claimed to be therapeutic in such pathologies as in their symptoms. In a particular embodiment the invention claim also the use of a betaine, preferably glycine betaine of formula $(CH3)_3N^+(CH2)COO^-$ and its pharmaceutically acceptable salts in order to prevent and/or treat phlebitis and venous insufficiency. Phlebitis and venous insufficiency are the manifestations of blood stagnation in the legs, known as venous congestion. Venous congestion is most evident when the legs are below the heart and least evident when they are at the heart level, for example when lying in bed. The inability to adequately move the blood that is below the heart upward towards the heart is known as venous insufficiency. This stagnant blood in the veins causes many of the symptoms that patients with veins complain of, such as swelling (edema), tired and heavy legs, throbbing in the legs, drawing pains and pain to touch. This is often relieved when the leg is elevated. Venous insufficiency can become chronic which is a more serious problem in that it increases the risk of ulceration in the legs and phlebitis (blood clots). With chronically high pressure on the veins, blood cells are thought to be forced out of the veins and capillaries and deposited into the surrounding tissue. The subsequent breakdown of red blood cells causes a dark 'rusty' look to the legs most often on the inner ankles and most importantly creates a barrier through which oxygen and nutrient transfer is lessened. This overlying skin is more prone to ulceration (holes in the skin) from any minor injury, such as a bump, scratch or bug bite. The betaines of the invention, preferably glycine betaine of formula $(CH3)_3N^+(CH_2)COO^-$ and its pharmaceutically acceptable salts in is thus claimed to be therapeutic in such pathologies as in their symptoms.

Phlebitis (blood clots) is the result of stagnant blood that has clotted within a vein. Phlebitis generally occurs when the already slowed blood flow in the varicose veins becomes slower or the bodies clotting mechanisms are stimulated. A long trip in a plane, a train or car, where the legs are not moving much is a common scenario for the start of phlebitis. It is a minor trauma to the legs that triggers clotting mechanisms. Certain clots can embolise from the leg veins and travel to the lungs or the heart triggering infarction or embolism. Those (blood clots) staying in the leg veins are also problematic both while in their acute phase and in years to come. Acutely they can cause pain, tenderness throbbing and discomfort. More long term, the leg and veins affected will suffer further venous insufficiency which generally worsens over future years. The betaines of the invention, preferably glycine betaine of formula $(CH3)_3N^+(CH_2)COO^-$ and its pharmaceutically acceptable salts in is thus claimed to be therapeutic in such pathologies as in their symptoms.

In a particular embodiment the invention claim also the use of a betaine, preferably glycine betaine of formula $(CH3)_3N^+(CH_2)COO^-$ and its pharmaceutically acceptable salts in order to prevent and/or treat blood flow disturbances in patients in need.

In a particular embodiment the invention claim also the use of a betaine, preferably glycine betaine of formula $(CH3)_3N^+(CH_2)COO^-$ and its pharmaceutically acceptable salts in order to prevent and/or treat in patient at need, especially in diabetic patients, one or more trouble selected from the group consisting of blood flow disturbances, thromboses, blood coagulation troubles, vasoconstriction troubles, peripheral arterial diseases, cardiovascular diseases, cerebrovascular diseases, renal diseases, intermittent claudication, diabetic neuropathy, diabetic angiopathy, cardiac troubles, varicose ulcers, acute coronary syndromes, hyperglycemia, glycated hemoglobin troubles, microcirculation troubles, erectile dysfunctions troubles and endothelial dysfunction troubles.

In another embodiment the invention claim also the use of a betaine, preferably glycine betaine of formula $(CH_3)_3N^+(CH_2)COO^-$ and its pharmaceutically acceptable salts in order to prevent and/or treat troubles linked to vasoconstriction.

Advantageously in said methods, an effective therapeutic amount of at least one therapeutically active compound selected from the group consisting of $(CH_3)_3N^+(CH_2)COO^-$, pharmaceutically active salts thereof and mixtures thereof is administered to said patient.

Preferably, the therapeutically active compound selected from the group consisting of $(CH_3)_3N^+(CH_2)COO^-$, pharmaceutically active salts thereof and mixtures thereof is administered to said patient with a dosage form selected from the group consisting of once daily administration forms and the twice daily administration forms.

According to advantageous embodiments, the therapeutically active compound selected from the group consisting of $(CH_3)_3N^+(CH_2)COO^-$, pharmaceutically active salts thereof and mixtures thereof is administered to said patient with an extended release dosage form.

According to a detail of embodiments, at least 1000 mg of the therapeutically active compound selected from the group consisting of $(CH_3)_3N^+(CH_2)COO^-$, pharmaceutically active salts thereof and mixtures thereof is daily administered to said patient as an immediate release dosage form.

According to a detail a preferred embodiment, at least 250 mg of the therapeutically active compound selected from the group consisting of $(CH_3)_3N^+(CH_2)COO^-$, pharmaceutically active salts thereof and mixtures thereof is daily administered to said patient as an extended release dosage form. Especially, from 250 mg to 3000 mg of the therapeutically active compound selected from the group consisting of $(CH_3)_3N^+(CH_2)COO^-$, pharmaceutically active salts thereof and mixtures thereof is daily administered to said patient as an extended release dosage form. For example, from 250 mg to 1000 mg of the therapeutically active compound selected from the group consisting of $(CH_3)_3N^+(CH_2)COO^-$ pharmaceutically active salts thereof and mixtures thereof is daily administered to said patient as an extended release dosage form.

According to another detail of a preferred embodiment, at least 250 mg of the therapeutically active compound selected from the group consisting of $(CH_3)_3N^+(CH_2)COO^-$, pharmaceutically active salts thereof and mixtures thereof is daily administered to said patient as an extended release dosage form, while at least 250 mg of the therapeutically active compound selected from the group consisting of $(CH_3)_3N^+(CH_2)COO^-$, pharmaceutically active salts thereof and mixtures thereof is daily administered to said patient as an immediate release dosage form.

Especially, at least one unit dosage form comprising an immediate release dosage portion of at least 250 mg of the therapeutically active compound selected from the group consisting of $(CH_3)_3N^+(CH_2)COO^-$, pharmaceutically active salts thereof and mixtures thereof and an extended release dosage portion of at least 250 mg of the therapeutically active compound selected from the group consisting of $(CH_3)_3N^+(CH_2)COO^-$, pharmaceutically active salts thereof and mixtures thereof is daily administered to said patient.

EXAMPLE 1

Effect of Betaine on Non Stimulated Blood Perfused on Activated Endothelial Cells.

We have studied the effect of betaine on platelets adherence and thrombus formation under laminar flow at high shear force (shear stress 60 dynes/cm$^2$) on a human micro vascular endothelial cell line (HMEC$^{-1}$) in resting condition or activated by PMA (200 µM, 45 minutes). Heparinised human blood was pre-labeled with mepacrine and exposed to vehicle only or to betaine (10, 20, 40, and 80 µg/ml) for 20 minutes before perfusion. The perfusion lasted for 3 min then the cells were fixed and the surface covered with thrombi was measured by image analysis obtained by confocal microscopy of the fluorescence of the thrombi.

Material and Methods

Platelet Adherence and Thrombus Formation.

Platelet adherence assay was performed according to the method described by Alevriadou et al. 1993 & Boccardo et al. 1997, with slight modifications. Human blood sampled on heparin (final concentration 10 IU/ml) was perfused through a laminar flow chamber using a piston pump. The flow chamber temperature is regulated at 37° C. and one of the glass walls is coated with a monolayer of endothelial cells on which the betaine treated blood is perfused.

Perfusion Chamber.

The dimensions of the perfusion chamber (length 30 mm, width 1 mm, and depth 150 µm) allow obtaining a wide range of shear force at low blood flow rates. The flow conditions are well established for such a setting and allow the flow to be laminar with very low Reynolds numbers (<10). A precise evaluation of the shear forces on the adhering surface is also performed using analysis software of fluid dynamics (CFD package FIDP, Fluid Dynamic International, Evanston, Ill.) that allows verifying the influence of inlet and outlet on flow velocity profile.

Adherence Assay on Endothelium.

A human micro vascular endothelial cell line of dermal origin (HMEC-1) was grown in MCDB 131 supplemented with FCS 10%, hydrocortisone 1 µg/ml, penicillin 100 U/ml, streptomycin 100 µg/ml, glutamine 2 mM and endothelial growth factor 50 µg/ml. For these experiences, the cells were spread on a glass coverslip and when confluent, they were stimulated with PMA (phorbol 12-myristate 13-acetate) in static conditions. After incubation the cells were perfused with the human blood. Heparinised blood was incubated with 10 µM mepacrine that gives a fluorescent staining (quinacrine dihydrochloride BP; Sigma Aldrich, St. Louis Mo.). Mepacrine concentrates in dense granules of platelets and in granules of leucocytes and at such concentration has no effect on normal function of platelets; any fluorescence in erythrocytes is quenched by hemoglobin.

The blood was pre-incubated for 5 minutes at 37° C. before perfusion. The device was filled with PBS pH 7.3, then blood perfusion was started and continued at a constant flow rate of 1500 sec-1 corresponding to a shear stress of 60 dynes/cm$^2$ mimicking the arterial condition that could be encountered in pathological conditions such as stenosis or arteritis). After 3 minutes, perfusion is stopped and the cell wail with the monolayer of endothelial cells is dehydrated and fixed in acetone for 20 minutes. The images of the platelets forming thrombi are recorded with an inverted laser confocal microscope (Insight plus; Meridian Instruments Inc, Okemos, Mich.). The surface occupied by each thrombus is evaluated using image analysis software (Image 1.61, NIH Bethesda, Md.). 15 fields systematically digitalized along the adherence surface were captured.

Results

Effect of betaine on thrombus formation on PMA stimulated HMEC-1 cells under flow (60 dynes/cm$^2$)

| Exp. n° | controls | PMA 200 nM 45' | PMA + betaine 20 µg/ml | PMA + betaine 40 µg/ml | PMA + betaine 80 µg/ml |
|---|---|---|---|---|---|
| #4 | 1649 | 4822 | 3059 | 3947 | 2451 |
| #6 | 1139 | 6243 | 1290 | 5146 | 1852 |
| #9 | 680 | 11843 | 1436 | 2470 | 4150 |
| #10 | 465 | 6538 | — | 1972 | 1077 |
| #12 | 845 | 5448 | — | 2795 | — |
| Mean ± Std Dev. | 955 ± 459 | 6979 ± 2880° | 1928 ± 982** | 3266 ± 1277* | 2388 ± 1305** |

Data are expressed as area covered by thrombi (µm$^2$/field)
HMEC-1: human microvascular endothelial cell line
PMA: phorbol 12-myristate 13-acetate
Blood was incubated with betaine for 20 minutes
°p < 0.01 Vs control
*p < 0.05,
**p < 0.01 Vs PMA Comments PMA stimulated endothelial cells express TNF α (Tumor Necrosis Factor Alpha) that induces the expression of different molecules such as prostaglandins, I-CAM, interleukins et various cytokines, all being inflammation markers. The interest of this experiment is that it mimics arteritis conditions with endothelial cells inflammation and consequently endothelial wall inflammation.

Indeed all different players of arteritis are present namely: blood, inflamed endothelial wall and shear forces. Control cells, meaning non inflamed cells since they were not PMA stimulated, show a limited tendency to adhere platelets despite the high shear force and there are no thrombus formation and by the way occluding conditions. On the other hand, once cells are inflamed, their tendency to form thrombus is remarkable and perfectly mimics the pathological conditions of an arteritis. In this model, betaine by bringing back to normal the adhesiveness of endothelial cells, acts on the expression of different molecules such as prostagiandins, I-CAM, interleukins as well as various cytokines and displays its activity on these markers of inflammation and thus on inflammation. This anti-inflammatory activity of betaine allows claiming its use in the treatment of occlusive or non-occlusive arteritis.

EXAMPLE 2

Effect of Betaine on Thrombin and Blood Viscosity

As blood viscosity increases, blood flow in whole body decreases, generating anoxia (oxygen depletion) and nutriment deprivation in different areas of the body. This too explains why betaine therapy is efficacious by increasing blood flow due to blood viscosity decreases. So the patients get more relief of their symptoms with this therapy. If coagulation mechanism does not stop correctly, then there is continuous thrombin generation and formation of soluble fibrin with results to an increased viscosity of the blood and a decreased blood flow in the body.

Moreover, in vitro, betaine counteract the effect induced by interleukin 1 and Tumor Necrosis Factor on polynuclear neutrophils, meaning slower motion, increased adhesiveness and liberation in excess of superoxide ions and hydrogen peroxides induced by these factors.

Similarly, betaine counteracts the reduction of erythrocyte deformability, a physiological perturbation whose role has been evidenced in numerous pathological processes, in particular in arteriopathy of lower limbs. The administration of glycine betaine caused a facilitation of red blood cell circulation, microcirculation being improved, without increasing the flow at the level of healthy zone to the detriment of ischemic zones.

a) In Vitro Aggregation on Animal Whole Blood Induced with Thrombin

To demonstrate the effect of betaine on thrombin we have made aggregation assay on whole blood. This technique on whole blood has the advantage that all blood elements are present, notably the red blood cells and the white blood cells these later being important factors in inflammation phenomenon. Though the deformability phenomenon, erythrocytes are also powerful actors of the pathologies related to arteritis.

Material and Methods

Blood from Wistar rat was sampled on citrate and dispensed in 2 samples for each animal, one sample was mixed with saline (control), the other with a solution of betaine at 5 mg/ml to yield a final concentration of betaine of 50 µg/ml of blood (treated) (10 µL of solution for 990 µL blood). The samples are then incubated with gentle agitation for 20 min. at 37° C. then thrombin is added (1 IU/ml) et the assay are made with an aggregometer (Chronolog 500).

Results

Amplitudes are expressed in ohms and les velocities en ohm/min.

| | NaCl 0.9% | | Bétaine 50 µg/ml | |
|---|---|---|---|---|
| | Amplitude Ω | Velocity Ω/min. | Amplitude Ω | Velocity Ω/min. |
| Rat 1 | 22 | 14 | 5 | 7 |
| Rat 2 | 17 | 18 | 3 | 5 |
| Rat 3 | 25 | 16 | 12 | 7 |
| Rat 4 | 18 | 16 | 8 | 5 |
| Rat 5 | 24 | 18 | 4 | 3 |
| Mean | 21.2 ± 3.56 | 16.4 ± 1.67 | 6.4 ± 3.65 | 5.4 ± 1.67 |

These results show the powerful activity of betaine toward thrombin. This latter playing a role in the pathologies described in the invention, notably blood viscosity and inflammatory phenomenon, it appears that the therapeutic use of betaine can be claimed in these pathologies as well as all the other pathologies involving thrombin.

b) Effect of Betaine in Healthy Volunteer After Oral Administration

The aim of this study was to evaluate the evolution of different hematological parameters after oral administration of betaine monohydrate (Betafin AP) 2×3 gr. for 4 days to 5 healthy volunteers.

Protocol

The tests were made in the "Service d'Hématologie Clinique" of Hôpital de la Citadelle in Liège, Belgium. The volunteers gave their informed consent before the initiation of the study.

The blood samples were take on Na-citrate by vein puncture in the arm of fasted donors at 9 a.m. on the first day (D1) to determine the basal values. Just after the sampling the volunteers took their first 3 g dose of betaine with their breakfast. The next dose of 3 g was taken on the same day, 12 hours later. On the 3 following days, the takes were continued morning and evening as well as a last take of 3 g in the morning of the last day (D5) fasted, 2 hours before the last blood sampling.

Results.

|  | Fibrinogen | | Thrombin/antithrombin | |
| --- | --- | --- | --- | --- |
|  | Jour 1 | Jour 5 | Jour 1 | Jour 5 |
| Donor 1 | 3.8 | 3.3 | 2.5 | 2.1 |
| Donor 2 | 3.3 | 3.1 | 2.9 | 2.2 |
| Donor 3 | 3.4 | 3 | 2.9 | 2.2 |
| Donor 4 | 2.9 | 2.2 | 3.2 | 2.6 |
| Donor 5 | 3.1 | 2.9 | 3.1 | 2.2 |
| Mean | 3.3 | 2.9 | 2.92 | 2.26 |
| Variation day 5 | −12% | | −23% | |

Comments.

A significant decrease was observed with all volunteers at the level of coagulation markers and blood viscosity. It appears that betaine administration decreases fibrinogen and by improving on blood fluidity allows a better blood flow. This decrease of blood viscosity allows a better irrigation of ischemic zones in pathologies related to arteritis. In the course of the same study, in 3 out of 5 donors, the binding of the von Willebrand factor to collagen as decreased indicating a therapeutic activity of betaine on the functional activity of the von Willebrand factor as well as pathologies linked to this factor.

c) In Vitro Generation of Thrombin on Human Blood

Protocol

These tests were made at the Cardiovascular Institute of Maastricht, The Netherlands. The blood from 5 healthy volunteers was sampled on Na-citrate (3.8%, 1:10) and centrifuged to yield Platelet Rich Plasma (PRP). This PRP was then incubated for 20 minutes with the addition of isotonic betaine (pH 7.0) or saline, each donor being its own control. The final concentration of betaine in the PRP was 100 µg/ml.

The generation of thrombin as determined using a Thrombogram®.

The results obtained show that in the presence of betaine, the generation of thrombin is reduced by 15 to 25% depending on the donor. This inhibitory activity on thrombin generation is comparable to those obtained in this model by the administration of aspirin or after the experimental administration of anti-glycoprotein Ib. The reduction of thrombin generation allows the reduction of the blood reactivity as well its ability to coagulate and its viscosity. This inhibitory activity of betaine by allowing a better blood circulation, blood being less viscous, reduces the arteritis and the damages linked to arteritis. The therapeutic use of betaine can also be claimed in all the pathologies involving an increased thrombin generation.

EXAMPLE 3

Inflammatory Challenge Caused by Oxidative Stress on Endothelial Wall, Effect of Betaine.

Arteritis are also pathological conditions were oxidative stress affects vascular walls, it was thus interesting to evaluate the effect of betaine in a free radical model. In this model the endothelial wall following a free radical attack presents the same reactions as in the pathologies of the invention.

Protocol

Hamsters weighing 120-130 g were used in these assays. The animals were injected with a Rose Bengal solution before exposing their femoral veins to a source of polarized green light to generate free radicals in situ. The polarized green light breaks down the Rose Bengal creating free radicals known to aggress the endothelial wall and produce conditions identical to those seen during inflammation, arteritis and from there on thrombosis. This experimental model perfectly depicts the interaction between the epithelium that becomes a pro-coagulant surface following this oxidative stress and the blood elements. Thrombus formation is quantified taking pictures every 10 sec of the femoral vain for 40 min (240 images per experiments). The calculation of the white light on each of the 240 images allows quantifying the size and the progression of the thrombus. The intensity of the white light corresponds to the number of platelets in the thrombus that also harbors leucocytes and erythrocytes.

The study substances are injected as a bolus (22 or 66 mg/kg) intra venous route at TO, followed by continuous infusion (22 or 66 mg/kg) for 40 minutes.

Results

|  | Controls | 22 mg/kg | 66 mg/kg |
| --- | --- | --- | --- |
| Hamster 1 | 413641 | 123074 | 70729 |
| #2 | 422820 | 47271 | 43315 |
| #3 | 449691 | 188041 | 56714 |
| #4 | 379908 | 121924 | 140621 |
| #5 | 452849 | 135688 | 162353 |
| #8 | 220109 | 477299 | 162477 |
| #7 | 359792 | 220730 | — |
| #8 | 268123 | 88407 | — |
| Means | 370 867 | 175304 | 106035 |

Comments

A decrease of −53% and −71% at 22 mg/kg and 66 mg/kg respectively of the recorded light was observed. It appears that the endothelial wall in the presence of betaine develops less pro-coagulant properties since the thrombus formed are much less important. In this model, it is demonstrated that the free radicals generated by the polarization of the Rose Bengal had no or little impact on platelet activity and/or blood rheology; this implies that betaine has a direct influence on the adhesiveness of the endothelial wall. Indeed the free radicals injuring the endothelial wall create the conditions of various pathologies such as degenerative inflammation, inflammation, cancer, occlusive inflammation as well as other procoagulant conditions linked to viral and/or bacterial infections. Betaine activity in this in vivo animal model demonstrates its efficacy on the pathologies involving aggression of the endothelial wall by free radicals. Oxidative stress on vessels walls in these experiments is similar to the stress seen in arteritis.

EXAMPLE 4

Measure In Vitro in Thromboelastography System (TEGC) of Blood Viscosity and Blood Coagulation Properties After Betaine Addition.

Protocol

Blood from 6 healthy volunteers was sampled and supplemented with various concentration of betaine and directly (less than four minutes post sampling) evaluated by Thrombelastogram TEG® (Haemoscope Corporation, Niles, Ill., USA). Betaine was studied at the following final concentration 0, 100, 250 and 500 µg/ml.

Results

| Betaine concentration | R (mm) | RK (mm) | K (mm) | MA (mm) | α Angle (°) |
|---|---|---|---|---|---|
| 0 µg/ml (NaCl 0.9%) | 30 | 34 | 4 | 68 | 63° |
| 100 µg/ml | 40 | 50 | 10 | 64 | 39° |
| 250 µg/ml | 46 | 55 | 9 | 61 | 45° |
| 500 µgl/ml | 95 | 111 | 16 | 68 | 34° |

Comments

Betaine effect was dose dependent and impacted almost all TEG parameters. An anticoagulant activity was demonstrated in these experiments, as well as a highly significant effect on the fibrin initial formation time (r) and consequently on blood viscosity. A notable activity is also demonstrated on α Angle that measures how fast the fibrin network forms in the blood and from there on blood viscosity and how slowly it could flow in the vessels. Betaine displays its effects on these parameters and by making blood less viscous tend to facilitate its flow and reduce its adhesion in the vascular system.

In this experimental setting, by reducing α Angle, betaine demonstrates too its fibrinolytic activity by rendering the formed clot more brittle and thus allowing its faster destruction (lysis).

The interest of this experiment lies in the fact that it uses native blood, meaning without addition of other anticoagulant substances but betaine and thus mimicking as closely as possible the physiological conditions that could be met in vivo after betaine administration.

EXAMPLE 5

Clinical Assay on Treadmill

Seven patients with arteritis and intermittent claudication, taking no other medication but aspirin (75 to 325 mg/day) were prescribed an oral dose of 4 gram/day of betaine monohydrate (Betafin Finnsugar) in two takes per day. The treatment lasted for 4 weeks.

The patient underwent a walking test on treadmill on the first and last day of the treatment to evaluate the effect of betaine.

The walking test on treadmill is standardized, speed is set to 3.2 Km/h and slope to 12%. It allows an evaluation of the distance walked until beginning of claudication, then the distances walked until stop meaning the moment when pain is such that it prevents the patient from continuing the walk.

Results

Five patients showed an improvement of the initial claudication distance by 25% and an improvement of the absolute walking distance by more than 30% thanks to the delay in the onset of pain and/or a more efficient walk. A delay in the onset of the first discomfort by 20% was also observed.

The 2 other patients displayed a less significant improvement of the total walking distance of almost 15%.

The questionnaire filled by each of the volunteers showed a general trend on improvement of comfort as well as a better feeling of the physical effort.

I claim:

1. A method for increasing the absolute claudication distance in a patient suffering of intermittent claudication or peripheral arterial disease with intermittent claudication, said method comprising administering to said patient, as a therapeutically active agent for increasing the maximal walking distance, a composition comprising as a single active ingredient a therapeutically effective amount of at least one therapeutically active compound selected from the group consisting of betaine of formula $(CH_3)_3N^+(CH_2)COO^-$, pharmaceutically active salts thereof and mixtures thereof, so as to increase said absolute claudication distance.

2. The method of claim 1, wherein the absolute claudication distance of said patient is increased by at least 10% with respect to the average walking distance of said patient before his treatment, said 10% increase corresponding to at least 20 meters and wherein the walking distance is determined by assessing the patient using a constant-load treadmill testing at a 12% grade inclination and speed of 3.2 km/h.

3. The method of claim 1, in which a therapeutically effective amount of at least one therapeutically active compound selected from the group consisting $(CH_3)_3N^+(CH_2)COO^-$, pharmaceutically active salts thereof and mixtures thereof is daily administered to said patient for at least 4 weeks.

4. The method of claim 1, in which an effective therapeutic amount of at least one therapeutically active compound selected from the group consisting of $(CH_3)_3N^+(CH_2)COO^-$, pharmaceutically active salts thereof and mixtures thereof is orally administered to said patient.

5. The method of claim 1, in which the therapeutically active compound selected from the group consisting of $(CH_3)_3N^+(CH_2)COO^-$, pharmaceutically active salts thereof and mixtures thereof is administered to said patient with a dosage form selected from the group consisting of the once daily administration forms and the twice daily administration forms.

6. The method of claim 1, in which the therapeutically active compound selected from the group consisting of $(CH_3)_3N^+(CH_2)COO^-$, pharmaceutically active salts thereof and mixtures thereof is administered to said patient with an extended release dosage form.

7. The method of claim 1, in which at least 1000 mg of the therapeutically active compound selected from the group consisting of $(CH_3)_3N^+(CH_2)COO^-$, pharmaceutically active salts thereof and mixtures thereof is daily administered to said patient as an immediate release dosage form.

8. The method of claim 1, in which at least 250 mg of the therapeutically active compound selected from the group consisting of $(CH_3)_3N^+(CH_2)COO^-$, pharmaceutically active salts thereof and mixtures thereof is daily administered to said patient as an extended release dosage form.

9. The method of claim 1, in which from 250 mg to 3000 mg of the therapeutically active compound selected from the group consisting of $(CH_3)_3N^+(CH_2)COO^-$, pharmaceutically active salts thereof and mixtures thereof is daily administered to said patient as an extended release dosage form.

10. The method of claim 1, in which from 250 mg to 1000 mg of the therapeutically active compound selected from the group consisting of $(CH_3)_3N^+(CH_2)COO^-$, pharmaceutically active salts thereof and mixtures thereof is daily administered to said patient as an extended release dosage form.

11. The method of claim 1, in which at least 250 mg of the therapeutically active compound selected from the group consisting of $(CH_3)_3N^+(CH_2)COO^-$, pharmaceutically active salts thereof and mixtures thereof is daily administered to said patient as an extended release dosage form, and at least 250 mg of the therapeutically active compound selected from the group consisting of $(CH_3)_3N^+(CH_2)COO^-$, pharmaceutically active salts thereof and mixtures thereof is daily administered to said patient as an immediate release dosage form.

12. The method of claim 1, wherein said therapeutically active compound selected from the group consisting of $(CH_3)_3N^+(CH_2)COO^-$, pharmaceutically active salts thereof and mixtures thereof is daily administered to said patient as at least one unit dosage comprising an immediate release dosage portion of at least 250 mg of the therapeutically active compound and an extended release dosage portion of at least 250 mg of the therapeutically active compound.

* * * * *